United States Patent [19]
Lipatova et al.

[11] 4,438,249
[45] Mar. 20, 1984

[54] BIODEGRADABLE POLYURETHANE UREA ACYL SEMICARBAZIDES FOR THE MANUFACTURE OF BIODEGRADABLE ALLOIMPLANTS

[76] Inventors: Tatyana E. Lipatova, ulitsa Rozy Ljuxemburg, 15. kv. 14; Dmitry V. Vasiichenko, ulitsa Serafimovicha, 7. kv. 26; Georgy A. Pkhakadze, ulitsa Vladimirskaya, 48a. kv. 16; Xenya L. Konoplitskaya, ulitsa Florentsii 10$^a$ kv. 102, all of Kiev, U.S.S.R.

[21] Appl. No.: 362,429

[22] Filed: Mar. 26, 1982

Related U.S. Application Data

[63] Continuation of Ser. No. 252,552, Apr. 9, 1981, abandoned.

[51] Int. Cl.$^3$ .................... C08G 18/10; C08G 18/38
[52] U.S. Cl. .......................................... 528/61; 528/76
[58] Field of Search ............................. 528/61, 76

[56] References Cited

PUBLICATIONS

Tanada et al., Chem. Abstr. 74, 113122n, 1971.
Naka et al., Chem. Abstr. 77, 165805u, 1977.
Negishi et al., Chem. Abstr. 71, 22833s, 1969.

Primary Examiner—Maurice J. Welsh
Attorney, Agent, or Firm—Ladas & Parry

[57] ABSTRACT

Polyurethane urea acyl semicarbazides for preparing biodegradable alloimplants having the general formula: $(-NH-R_1-CONHNHCONH-R_2-NH-CO-O-R_3-CONH-R_2-NH-CO-)_n$ where n=5–24; $R_1$ is selected from the group consisting of

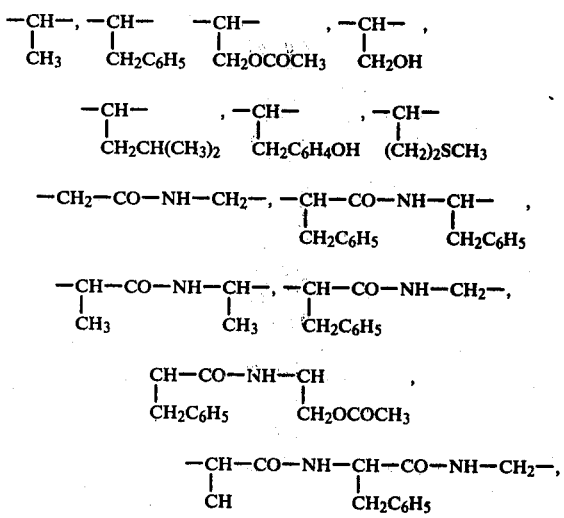

$R_2$ is selected from the group consisting of $-(CH_2)_6-$, $-C_6H_4-CH_2-C_6H_4-$; $R_3$ is selected from the group consisting of $-(CH_2)_4-O-_{14}$, $-(CH_2)_4-O-_{21}$.

2 Claims, No Drawings

BIODEGRADABLE POLYURETHANE UREA ACYL SEMICARBAZIDES FOR THE MANUFACTURE OF BIODEGRADABLE ALLOIMPLANTS

This is a continuation of application Ser. No. 252,552, filed Apr. 9, 1981, and now abandoned.

BACKGROUND OF THE INVENTION

1. Field of the Invention

The present invention relates to polymers, and more particularly to novel chemical compounds pertaining to polymer products of isocyanates, namely to polyurethane urea acyl semicarbazides.

The compounds of the present invention may be used in restorative surgery for preparing biodegradable alloimplants intended to remove the defects of organs and tissues.

At present, alloimplants made from biodegradable synthetic polymer materials are usually used for such purposes. After removing the tissue defects, such alloimplants should, in the course of time, provide for the regeneration of the tissues and then be removed from the organism in the form of biodegradation products. At present, the biodegradation of the alloimplants made from synthetic polymer materials is provided for and controlled by introducing the required number of labile links in the main chain of a polymer. However, it is rather difficult to precisely control the time of biodegradation in this case, because the enzymous composition of the tissues is neglected.

Attempts have been made to control the biodegradation time of the polymer materials by increasing the concentration of labile links in the main chain of a polymer by changing the chemical nature of the side groups of the polymer chain as well as by controlling the hydrophilic-and-hydrophobic balance of the polymer macromolecules.

Rather prospective in today's medicine is the use of compounds based on polyurethanes whose chemical and physical properties can be goal-orientedly varied in a wide range.

For example, known in the art is a cross-linked formed polyurethane (see French Patent No 2,318,183) which is prepared in the result of interaction between water and polyurethane prepolymer blocked by isocyanate. However, the destruction of said foamed polyurethane occurs as a result of hydrolysis of an ester group in the main chain of the initial prepolymer, i.e. the enzymous properties of the tissues are ignored.

Thus, the above facts prove that the problem has not been adequately solved up till now.

SUMMARY OF THE INVENTION

The principal object of the present invention is to provide polyurethanes for preparing biodegradable alloimplants which degrade in the result of a specific enzymous hydrolysis both in water solutions of proteolytic enzymes and in a living organism.

The proposed polyurethane urea acyl semicarbazides are novel compounds and have not been described in literature.

According to the invention, said compounds are of the following general formula:

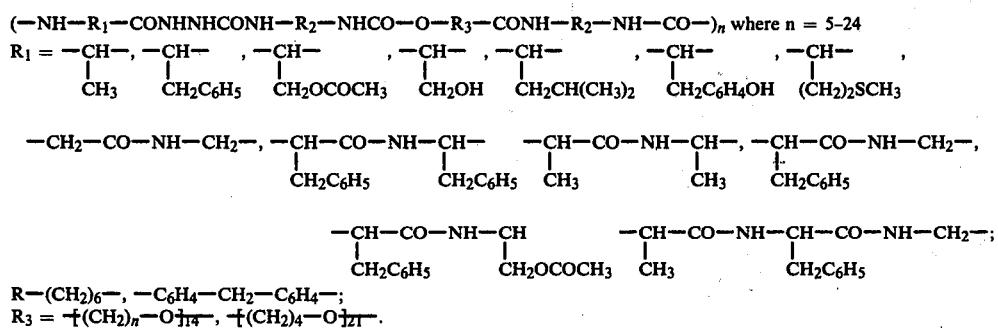

of the tissues is neglected.

Attempts have been made to control the biodegradation time of the polymer materials by increasing the The compounds of the present invention are given in Table 1.

TABLE 1

| No. | Amino acid or peptide contained in the main chain of polymer | $R_1$ | $R_2$ | $R_3$ |
|---|---|---|---|---|
| 1 | L-alanine | —CH—<br>\|<br>CH$_3$ | —(CH$_2$)$_6$— | $\dashv(CH_2)_4$—O$\dashv_{14}$— |
| 2 | L-phenylalanine | —CH—<br>\|<br>CH$_2$C$_6$H$_5$ | " | " |
| 3 | O—acetyl-L-serine | —CH—<br>\|<br>CH$_2$OCOCH$_3$ | " | " |
| 4 | L-leucine | —CH—<br>\|<br>CH$_2$CH(CH$_3$)$_2$ | " | " |

TABLE 1-continued

| No. 1 | Amino acid or peptide contained in the main chain of polymer 2 | R$_1$ 3 | R$_2$ 4 | R$_3$ 5 |
|---|---|---|---|---|
| 5 | L-methionine | —CH—<br>\|<br>(CH$_2$)$_2$SHC$_3$ | " | " |
| 6 | L-tyrosin | —CH—<br>\|<br>CH$_2$C$_6$H$_4$OH | " | " |
| 7 | DL-phenylalanine | —CH—<br>\|<br>CH$_2$C$_6$H$_5$ | " | " |
| 8 | Glycyl-glycine | —CH$_2$—CO—NH—CH$_2$— | " | " |
| 9 | L-alanyl-L-alanine | —CH—CO—NH—CH—<br>\|             \|<br>CH$_3$       CH$_3$ | " | " |
| 10 | L-phenylalanyl-L-phenylalanine | —CH—CO—NH—CH—<br>\|             \|<br>CH$_2$C$_6$H$_5$  CH$_2$C$_6$H$_5$ | " | " |
| 11 | L-phenylalanyl-o-acetyl-L-serine | —CH—CO—NH—CH—<br>\|             \|<br>CH$_2$C$_6$H$_5$  CH$_2$OCOCH$_3$ | " | " |
| 12 | L-phenylalanyl-glycine | —CH—CO—NH—CH$_2$—<br>\|<br>CH$_2$C$_6$H$_5$ | —(CH$_2$)$_6$— | -(-(CH$_2$)$_4$—O-)$_{14}$- |
| 13 | L-alanyl-L-phenylalanyl-glycine | —CH—CO—NH—CH—CONH—CH$_2$—<br>\|            \|<br>CH$_3$        CH$_2$C$_6$H$_5$ | " | " |
| 14 | L-alanine | —CH—<br>\|<br>CH$_3$ | C$_6$H$_4$CH$_2$—C$_6$H$_4$ | " |
| 15 | L-phenylalanine | —CH—<br>\|<br>CH$_2$C$_6$H$_5$ | " | " |
| 16 | L-serine | —CH—<br>\|<br>CH$_2$OH | " | " |
| 17 | O—acetyl-L-serine | —CH—<br>\|<br>CH$_2$OCOCH$_3$ | " | " |
| 18 | L-alanyl-L-alanine | —CH—CO—NH—CH—<br>\|             \|<br>CH$_3$       CH$_3$ | " | " |
| 19 | L-phenylalanyl-L-phenylalanine | —CH—CO—NH—CH—<br>\|             \|<br>CH$_2$C$_6$H$_5$  CH$_2$C$_6$H$_5$ | " | " |
| 20 | L-phenylalanyl-glycine | —CH—CO—NH—CH$_2$—<br>\|<br>CH$_2$C$_6$H$_5$ | " | " |
| 21 | L-alanyl-L-phenylalanyl-glycine | —CH—CO—NH—CH—CO—NH—CH$_2$<br>\|            \|<br>CH$_3$        CH$_2$C$_6$H$_5$ | —C$_6$H$_4$CH$_2$C$_6$H$_4$— | -(-(CH$_2$)$_4$—O-)$_{14}$- |
| 22 | L-phenylalanine | —CH—<br>\|<br>CH$_2$C$_6$H$_5$ | —(CH$_2$)$_6$— | -(-(CH$_2$)$_4$—O-)$_{21}$- |

The above compounds are white flakes or powders which are soluble in dimethyl formamide, hexamethyl phosphoric triamide, dimethyl sulfoxide and in the given in Table 2.

TABLE 2

| No. of compound in accordance with Table 1 | Interval of melting temperatures, °C. | Intrinsic viscosity [η], dl/g | Molecular mass, Mm | Degree of polimerization, (n) | Results of elementary analysis | | | | | |
|---|---|---|---|---|---|---|---|---|---|---|
| | | | | | Nitrogen, % | | Carbon, % | | Hydrogen, % | |
| | | | | | Found | Calcd | Found | Calcd | Found | Calcd |
| 1 | 2 | 3 | 4 | 5 | 6 | 7 | 8 | 9 | 10 | 11 |
| 1 | 143–152 | 0.33 | 17200 | 12 | 5.62 | 6.80 | 61.56 | 61.74 | 10.18 | 10.36 |
| | | | | | 5.65 | | 61.62 | | 10.34 | |
| 2 | 106–130 | 0.30 | 15000 | 10 | 6.02 | 6.47 | 63.63 | 63.44 | 10.05 | 10.11 |
| | | | | | 6.03 | | 63.80 | | 10.11 | |
| 3 | 98–120 | 0.34 | 17900 | 12 | 5.59 | 6.74 | 62.08 | 62.56 | 10.29 | |
| | | | | | 5.42 | | 62.27 | | 10.34 | |
| 4 | 88–100 | 0.34 | 17900 | 12 | 5.66 | 6.62 | 62.39 | 62.47 | 10.50 | 10.48 |
| | | | | | 5.62 | | 62.59 | | 10.68 | |
| 5 | 97–115 | 0.33 | 17200 | 12 | 5.40 | 6.54 | 61.81 | 60.87 | 9.88 | 10.22 |
| | | | | | 5.19 | | 62.02 | | 10.08 | |
| 6 | 192–198 | 0.31 | 15700 | 10 | 5.94 | 6.39 | 61.20 | 62.57 | 10.18 | 9.98 |
| | | | | | 5.84 | | 61.31 | | 10.05 | |
| 7 | 136–182 | 0.36 | 19500 | 13 | 6.34 | 6.47 | 62.05 | 63.44 | 9.50 | 10.11 |
| | | | | | 6.32 | | 62.19 | | 9.70 | |
| 8 | 205–220 | 0.27 | 12900 | 9 | 7.17 | 7.56 | 61.47 | 60.80 | 10.32 | 10.14 |
| | | | | | 7.24 | | 61.65 | | 10.34 | |
| 9 | 193–197 | 0.35 | 18700 | 12 | 6.58 | 7.41 | 61.32 | 61.22 | 9.92 | 10.20 |
| | | | | | 6.69 | | 61.37 | | 10.12 | |
| 10 | 167–171 | 0.22 | 9600 | 6 | 6.66 | 6.74 | 64.22 | 64.33 | 9.90 | 9.77 |
| | | | | | 6.87 | | 64.38 | | 9.93 | |
| 11 | 115–141 | 0.25 | 11600 | 7 | 6.36 | 6.81 | 61.85 | 62.07 | 9.66 | 9.74 |
| | | | | | 6.38 | | 62.01 | | 9.67 | |
| 12 | 112–146 | 0.57 | 37500 | 24 | 6.71 | 7.14 | 62.47 | 62.67 | 10.00 | 9.94 |
| | | | | | 6.69 | | 62.67 | | 10.20 | |
| 13 | 164–176 | 0.35 | 18700 | 11 | 6.41 | 7.67 | 61.15 | 61.38 | 9.90 | 9.81 |
| | | | | | 6.53 | | 61.34 | | 9.84 | |
| 14 | 195–201 | 0.31 | 15700 | 10 | 5.38 | 6.12 | 64.55 | 65.18 | 8.24 | 8.74 |
| | | | | | 5.76 | | 64.63 | | 8.34 | |
| | | | | | 5.59 | | 64.57 | | 8.36 | |
| 15 | 138–140 | 0.40 | 22600 | 14 | 5.22 | 5.83 | 66.08 | 66.52 | 8.44 | 8.70 |
| | | | | | 5.04 | | 66.16 | | 8.60 | |
| | | | | | | | | | 8.60 | |
| 16 | 210–220 | 0.40 | 22600 | 14 | 5.54 | 6.06 | | 65.54 | 8.27 | 8.53 |
| | | | | | 5.41 | | 65.14 | | 8.44 | |
| | | | | | 5.46 | | 64.94 | | 8.32 | |
| 17 | 208–216 | 0.42 | 24300 | 15 | 5.11 | 5.90 | 64.49 | 64.35 | 8.37 | 8.62 |
| | | | | | 5.14 | | 64.56 | | 8.48 | |
| | | | | | 5.17 | | 64.82 | | 8.61 | |
| 18 | 225–238 | 0.34 | 17900 | 11 | 5.83 | 6.69 | 64.99 | 64.57 | 8.74 | 8.67 |
| | | | | | 5.93 | | 65.26 | | 8.61 | |
| | | | | | 5.91 | | 65.41 | | 8.35 | |
| 19 | 200–201 | 0.38 | 21000 | 12 | 5.50 | 6.14 | 64.83 | 67.08 | 8.65 | 8.50 |
| | | | | | 5.57 | | 65.01 | | 8.82 | |
| | | | | | 5.54 | | 65.22 | | 8.52 | |
| 20 | 160–161 | 0.33 | 17200 | 10 | 5.38 | 6.12 | 64.55 | 65.18 | 8.24 | 8.74 |
| | | | | | 5.76 | | 64.63 | | 8.34 | |
| | | | | | 5.59 | | 64.57 | | 8.36 | |
| 21 | 166–167 | 0.22 | 9600 | 5.0 | 5.11 | 6.97 | 64.27 | 65.13 | 8.65 | 8.12 |
| | | | | | 5.22 | | 64.33 | | 8.54 | |
| | | | | | 5.31 | | 64.71 | | | |
| 22 | 140–142 | 0.50 | 31100 | 15 | 4.13 | 4.86 | 64.41 | 64.95 | 10.19 | 9.35 |
| | | | | | 4.18 | | 64.81 | | 10.37 | |
| | | | | | 4.10 | | 64.39 | | 10.10 | |

As far as the data represented in Table 2 are concerned, the following is to be noted.

Intrinsic viscosity ([η]) was measured in solutions of the polymer in dimethyl formamide at a temperature of 25° C. and within the interval of concentration of 1.0 to 0.4% by weight.

Molecular mass (Mm) of the compounds of the present invention was calculated in accordance with the following formula:

$$[\eta] = 3.58 \cdot 10^{-4} \cdot Mm^{0.7}$$

where Mm is a weight average molecular mass in carbon units (see A. P. Grekov, S. A. Sukhorukova, "Polimery na osnove gidrazina", Kiev, Izdatelstvo "Naukova dumka", p.98, 1976).

Molecular mass of the compounds of the present invention was from 9,000 to 37,000 carbon units.

The frequencies of the infrared sprectra in the range of 3800 cm$^{-1}$ to 700 cm$^{-1}$ of the claimed polyurethane urea acyl semicarbazides are given in Table 3

TABLE 3

| No. of compound according to Table 1 | Stretching vibrations of C—O ether bond, cm$^{-1}$ | Stretching vibrations of O=C—O urethane bond, cm$^{-1}$ | Stretching vibrations of C=O urethane bond, cm$^{-1}$ | Stretching vibrations of C=O urea bond, cm$^{-1}$ | Stretching vibrations of NH urethane bond, cm$^{-1}$ | deformation vibration of NH urethane bond, cm$^{-1}$ | deformation plane vibration of benzene, cm$^{-1}$ |
|---|---|---|---|---|---|---|---|
| 1 | 2 | 3 | 4 | 5 | 6 | 7 | 8 |
| 1 | 1115 | 1250 | 1725 | 1660 | 1540 | 3320 | — |
| 2 | 1115 | 1250 | 1710 1720 | 1660 | 1540 | 3320 | — |
| 3 | 1115 | 1250 | 1710 1720 | 1660 | 1540 | 3320 | — |
| 4 | 1115 | 1250 | 1710 | 1660 | 1540 | 3310 | — |
| 5 | 1115 | 1250 | 1720 1710 | 1660 | 1540 | 3335 | — |
| 6 | 1115 | 1250 | 1720 1710 | 1660 | 1540 | 3330 | — |
| 7 | 1115 | 1250 | 1710 1720 | 1660 | 1540 | 3320 | — |
| 8 | 1120 | 1255 | 1710 1720 | 1660 | 1570 | 3320 3340 | — |
| 9 | 1120 | 1255 | 1720 | 1665 | 1570 | 3325 | — |
| 10 | 1120 | 1255 | 1710 1720 | 1650 | 1570 | 3300 | — |
| 11 | 1125 | 1250 | 1725 | 1660 | 1570 | 3330 | — |
| 12 | 1120 | 1250 | 1720 | 1660 | 1570 | 3325 3340 | — |
| 13 | 1115 | 1260 | 1705 1720 | 1660 | 1550 | 3280 3310 | — |
| 14 | 1115 | 1230 | 1705 1725 | 1660 | 1540 1550 | 3300 | 1600 |
| 15 | 1115 | 1225 | 1705 1730 | 1660 | 1540 1550 | 3300 | 1605 |
| 16 | 1115 | 1225 | 1730 | 1660 | 1540 1550 | 3300 | 1605 |
| 17 | 1115 | 1230 | 1710 1730 | 1660 | 1550 | 3300 | 1605 |
| 18 | 1120 | 1230 | 1730 | 1660 | 1550 | 3300 | 1605 |
| 19 | 1115 | 1230 | 1705 1725 | 1660 | 1540 1550 | 3300 | 1605 |
| 20 | 1115 | 1230 | 1730 | 1660 | 1540 1550 | 3300 | 1605 |
| 21 | 1115 | 1225 | 1710 1725 | 1660 | 1545 1555 | 3300 | 1600 |
| 22 | 1115 | 1250 | 1720 | 1660 | 1560 | 3320 | — |

Mechanical properties of the polyurethanes of the present invention are given in Table 4.

TABLE 4

| No. of compound in accordance with Table 1 | Stress, n/m² · 10⁶ | Relative deformation, % | Elasticity modulus, n/m² · 10⁶ |
|---|---|---|---|
| 1 | 2 | 3 | 4 |
| 1 | 5.70 | 200 | 5.35 |
| 2 | 5.57 | 140 | 5.44 |
| 3 | 7.39 | 890 | 3.33 |
| 4 | 2.17 | 440 | 2.04 |
| 5 | 1.46 | 170 | 1.35 |
| 6 | 3.64 | 180 | 3.46 |
| 7 | 4.25 | 720 | 1.81 |
| 8 | 5.88 | 150 | 5.62 |
| 9 | 8.64 | 120 | 8.35 |
| 10 | 5.95 | 130 | 5.55 |
| 11 | 4.79 | 490 | 3.70 |
| 12 | 3.67 | 140 | 3.44 |
| 13 | 7.87 | 1280 | 4.39 |
| 14 | 11.89 | 980 | 5.65 |
| 15 | 11.13 | 1340 | 3.53 |
| 16 | 21.12 | 1570 | 5.39 |
| 17 | 14.57 | 1040 | 7.28 |
| 18 | 15.09 | 633 | 8.49 |
| 19 | 16.04 | 1150 | 6.89 |
| 20 | 13.17 | 800 | 6.70 |
| 21 | 4.34 | 330 | 2.81 |
| 22 | 3.59 | 760 | 2.89 |

As far as the data represented in Table 4 are concerned, the following is to be noted.

Samples made from the compounds of the present invention were tested according to conventional testing procedures (see D. F. Williams, R. Roaf, Implants in Surgery, 1973, W. B. Saunders Company Ltd. London, Philadelphia, Toronto).

To determine the stress, relative deformation, and elasticity modulus (Young's modulus of elasticity), samples which had the form of 30×4×0.3 mm polymer films were subjected to breaking test at a breaking speed of 10 mm/min.

The polymer films were made from 20% solutions of the proposed polyurethane urea acyl carbazides in dimethyl formamide on a polished substrate from fluorine plastic by way of evaporating the solvent at a temperature of 40° to 60° C. and a residual pressure of 6 to 10 hPa for 6 to 8 hours.

The compounds of the present invention can biodegrade both under the influence of proteolytic enzymes and in a living organism.

To investigate the effect of the proteolytic enzymes upon polyurethane urea acyl semicarbazides of the present invention, there were selected two enzymes, namely trypsin and chymotrypsin. Used as substrates acted upon by said enzymes were two polyurethanes urea acyl semicarbazides: polyurethane containing links of dipeptide of glycylglycine in the main polymer chain, and polyurethane containing links of dipeptide of L-phenylalanyl-O-acetyl-L-serine in the main polymer chain.

The above polymers were ground in a ball mill at a temperature of liquid nitrogen. According to control measurements, the viscosity of said polymers does not change under the action of low temperatures.

The ground polymers were placed in weighing bottles (two weighing bottles for each polymer, the weighed portion of the polymer in each weighing bottles being 1 g). Each of the polymers was poured over with 25 ml of a freshly prepared 0.005% solution of trypsin and chymotrypsin in a phosphate buffer having a pH of 7.8, whereupon the polymers were held in a thermostat at a temperature of 37° C. Every 12 hours the solutions of said enzymes were replaced by freshly prepared ones. The experiment lasted 14 days. Thereafter the intrinsic viscosity of the polymers that had been subjected to the action of the enzymes was measured as described hereinbelow.

The results of measuring the intrinsic viscosity of said polymers as well as the results of determination of molecular masses and the degree of polymerization which were calculated by the values of the intrinsic viscosity are given in Table 5.

TABLE 5

The effect of solutions of proteolytic enzymes upon intrinsic viscosity [η], molecular mass (Mn), and the degree of polymerization (n) of the polyurethanes.

| Dipeptide contained in the main polymer chain | L-phenyalanyl-O-acetyl-L-serine | | | Glycyl-glycine | | |
|---|---|---|---|---|---|---|
| Enzyme | [η] dl/g | Mn | (n) | [η] dl/g | Mn | (n) |
| Trypsin | 0.25 | 11500 | 7 | 0.26 | 12200 | 8 |
| Chymotrypsin | 0.18 | 7200 | 4 | 0.27 | 12900 | 9 | noted in the samples being tested. It is known that the proteolytic enzymes do not cause hydrolytic degradation of polyurethanes which do not contain such labile sections as links of peptides and amino acids in the main polymer chain/see T. E. Lipatova, G. A. Pkhakadze, Primenenie polimerov v khirurgii, Kiev, Izdatelstvo "Naukova Dumka", 1977, pp. 60–61/).

Biodegradation of the polyurethane of the present invention in a living organism was experimentally studied on Shinshilla rabbits of 2 to 3 kg in weight.

Each of the polymer samples, 20×10×0.3 mm films prepared as described above, were implanted to rabbits subcutaneously. In each set of experiments there were used 12 animals for each sample of the polymers. After implantation, the animals were taken out of the experiment at the end of one week, then at the end of two weeks, then at the end of one month, and at last at the end of 3 months (each time 3 rabbits were taken out of the experiment). Then the tissues adjacent the implant were cut out and fixed in 10% neutral formalin. After the fixation, the sections of said tissues having a thickness of 10 to 12μ where colored with hematoxylinposin and according to Van Gieson method, whereupon morphological response of the tissues to said samples was studied under microscope. This response manifested itself as an aseptic inflammation which faded away in 2 to 4 weeks following the operation, which proves that the tested polymer implants had no histotoxic action.

The samples implanted to the animals were tested to determine the value of intrinsic viscosity thereof as well as the values of molecular masses and degree of polymerization, calculated with the aid of said value of intrinsic viscosity. The results are given in Table 6.

TABLE 6

| No of compound in accordance with Table 1 | Initial sample | | | Implantation period | | | | | | | | |
|---|---|---|---|---|---|---|---|---|---|---|---|---|
| | | | | 2 weeks | | | 1 month | | | 3 months | | |
| | [η] dl/g | Mm | (n) | [η] dl/g | Mm | (n) | [η] dl/g | Mm | (n) | [η] dl/g | Mm | (n) |
| 11 | 0.25 | 11500 | 7 | 0.25 | 11500 | 7 | 0.15 | 5500 | 4 | 0.130 | 4500 | 3 |
| 8 | 0.27 | 12900 | 9 | 0.25 | 11900 | 8 | 0.220 | 9600 | 7 | 0.210 | 9000 | 6 |
| 2 | 0.30 | 15000 | 10 | 0.240 | 10900 | 7 | 0.230 | 10200 | 7 | 0.220 | 9600 | 6 |
| 3 | 0.340 | 17900 | 12 | 0.030 | 14700 | 10 | 0.280 | 13200 | 9 | 0.240 | 11000 | 7 |

Note:
Similar decrease in values of the above characteristics due to the increase in the implantation period is also true for the rest of the compounds of the present invention.

The data of Table 5 prove that said solution of chymotrypsin encourages a decrease in the molecular mass of the polyurethane containing links of L-phenylalanyl-O-acetyl-L-serine in the main chain, which is in good agreement with the specific action of chymotrypsin upon substrates containing aromatic amino acid (chymotrypsin specifically breaks peptide bonds formed by the carboxyl group of aromatic natural amino acids /α-L-amino acids/). At the same time, the solution of trypsin does not influence this polymer considerably, since this enzyme specifically breaks peptide bonds formed by the carboxyl group of lysine or arginine and thus is non-specific for this polymer. For this same reason, said solutions of trypsin and chymotrypsin do not effect much the polyurethane which contains links of glycyl-glycine in the main polymer chain. (For comparison reasons, there was studied the influence of phosphate buffer solutions having a pH of 4.0, 7.8, and 8.0 upon films from polyurethane urea acyl semicarbazides for 3 months, the buffer solutions being replaced by freshly prepared ones every day. No changes were The data of Table 6 show that the longer are disposed the samples of alloimplants of tested polyurethane urea acyl semicarbazides within the animal organism, the more appreciably the molecular mass of the compounds of the present invention decreases, which proves that biodegradation of said samples occurs.

It is to be noted that the biodegradation of the polyurethane urea acyl semicarbazides of the present invention occurs at different rates. The biodegradation rate depends on the presence of specific links of amino acids or peptides as well as on an enzymatic spectrum of a biological object, acting upon the alloimplants prepared from the compounds of the present invention.

The destruction of the compounds of the present invention in the living organism is also confirmed by the results obtained in the course of studying the morphology of these compounds by electron microscopy.

The above polymer samples, after being introduced into the animal organism and removed therefrom, were subjected to mechanical testing to determine the stress, relative deformation, and elasticity modulus thereof.

The results of testing are given in Table 7.

TABLE 7

| No. of compound in accordance with Table 1 Implantation period 1 | 11 | | | 8 | | |
|---|---|---|---|---|---|---|
| | stress in n/m² 2 | relative deformation in % 3 | elasticity modulus in n/m² 4 | stress in n/m² 5 | relative deformation in % 6 | elasticity modulus in n/m² 7 |
| Initial sample | 4.74 | 390 | 3.70 | 5.88 | 150 | 5.62 |
| one week | 3.52 | 150 | 3.34 | — | — | — |
| two weeks | 3.36 | 130 | 3.18 | — | — | — |
| one month | 3.04 | 100 | 2.94 | 3.62 | 50 | — |
| three months | 2.80 | 50 | — | the film has degraded | | |

The data of Table 7 show that the longer are disposed within the animal organism the alloimplants prepared from said compounds, the worse are their mechanical properties, which proves that there occurs biodegradation of said alloimplants. Thus, we believe that the drop in the relative deformation of the samples being tested may be related to the decrease in the molecular mass of said polymers and, consequently, to the decrease in the size of their macromolecules, which impairs the flexibility of the latter and brings about a drop in elasticity of the polymer samples being tested.

To compare the biodegradation of the compounds of the present invention under the influence of protelytic enzymes and the biodegradation of the same compounds in the living organism, there were taken infrared spectra of the samples which had been subjected to the action of proteolytic enzymes, trypsin and chymotrypsin, and infrared spectra of those samples which had been implanted into the living organism for various periods.

Infrared spectra of said compounds were taken in the absorption region of 3800 to 700 $cm^{-1}$.

The comparison of the infrared spectra of said polymer samples made it possible to reveal some differences in the variation of the intensity of carbonyl absorption bands in the range of 1620 to 1720 $cm^{-1}$. The quantitative calculation of the absorption bands in the region of 1750 to 1600 $cm^{-1}$ was carried out in accordance with the "internal standard" technique, taking into account the band width and the infrared diffusion from the polymer samples.

Used as the "internal standard" was stretching band CH. The relative intensity of the carbonyl absorption band (R) was determined as a ratio between the optical density of the band being tested and the optical density of the stretching band CH.

The values of the relative intensity of the carbonyl absorption bands are given in Table 8.

TABLE 8

| No. of compound in accordance with Table 1 | 11 | | 8 | | | |
|---|---|---|---|---|---|---|
| Media acting upon said compounds | 1720 $cm^{-1}$ R bands | 1660 $cm^{-1}$ R bands | 1720 $cm^{-1}$ R bands | 1660 $cm^{-1}$ R bands | 1640 $cm^{-1}$ R bands | 1620 $cm^{-1}$ R bands |
| Initial compound | 2.5 | 1.74 | 1.92 | 1.51 | 1.29 | 1.14 |
| Aqueous solution of trypsin | 2.5 | 1.75 | 2.01 | 1.56 | 1.38 | 1.12 |
| Aqueous solution of chymotrypsin | 2.46 | 1.48 | 1.92 | 1.6 | 1.27 | 1.15 |
| Within the rabbit's organism | | | | | | |
| 2 weeks | 2.48 | 1.70 | — | — | — | — |
| 1 month | 1.08 | 1.50 | 2.01 | 1.54 | 1.23 | 1.12 |
| 3 months | 1.39 | 1.21 | 2.0 | 1.54 | 1.12 | 1.0 |
| 6 months | — | — | 1.18 | 1.46 | 1.06 | 0.87 |

The data represented in Table 8 show that the influence of chymotrypsin upon the polyurethane containing the links of L-phenylalanyl-O-acetyl-L-serine in the main polymer chain results in a decrease in the relative intensity of the carbonyl absorption band in the region of 1660 $cm^{-1}$, which is characteristic of the stretching vibration of amido (peptide) bond /see M. Mashima, Infrared Absorption Spectra of some Monoacid Hydrazides, Bull. Chem. Soc. Japan, 35, 1882-1889, 1962/.

When acted upon by trypsin, the polyurethane containing the links of L-phenylalanyl-O-acetyl-L-serine in the main polymer chain does not exhibit any changes in the infrared spectrum. When acted upon by trypsin and chymotrypsin, the polyurethane containing the links of glycyl-glycine in the main polymer chain does not exhibit any changes in the infrared spectrum either.

The obtained data are in good accordance with the specificity of the influence of said enzymes upon substrates and with the data characterizing the intrinsic viscosity of these same polymer samples.

It can be seen from Table 8 that the alloimplant prepared from the polyurethane containing the links of L-phenylalanyl-O-acetyl-L-serine in the main polymer chain exhibits, after being introduced into the living organism for various periods of time, a decrease in the relative intensity of the absorption bands in the region of 1660 cm$^{-1}$ (peptide bond) and in the region of 1720 cm$^{-1}$ (urethane bond), which means the destruction of the peptide bond and urethane bond.

The alloimplant prepared from polyurethane containing the links of glycyl-glycine in the main polymer chain exhibits, after being introduced into the living organism for various periods of time, a decrease in the intensity of the absorption bands in the region of 1620 cm$^{-1}$ (semicarbazide bond) and in the region of 1640 cm$^{-1}$ (peptide bond), which corresponds to the destruction of the semicarbazide bond and peptide bond /see M. Mashima, Infrared Absorption Spectra of some Monoacid Hydrazides, Bull. Chem. Soc. Japan, 35,1882–1889, 1962/.

The decrease in the intensity of the absorption bands of said polymer in the region of 1720 cm$^{-1}$ (urethane bond) and in the region of 1660 cm$^{-1}$ (peptide bond) is less distinct than in the polyurethane containing the links of L-phenylalanyl-O-acetyl-L-serine in the main polymer chain.

It is to be noted that in the infrared spectrum of the polyurethane containing links of L-phenylalanyl-O-acetyl-L-serine in the main polymer chain there is no absorption band of 1620 cm$^{-1}$, which, in our opinion, stems from intramolecular interactions of the acylated hydroxyl group of serine and hydrazide group.

Thus the conclusion can be drawn that in the living organism the biodegradation of the compounds of the present invention occurs predominantly as an enzymatic hydrolysis due to the destruction of peptide bonds.

It is necessary that the degradable alloimplants which are in the immediate vicinity from blood possess stable thromboresistant properties.

There were investigated thromboresistant properties of polyurethane containing the links of L-phenylalanyl-O-acetyl-L-serine in the main polymer chain and of polyurethane containing the links of L-phenylalanine in the main polymer chain. The thromboresistant properties of said polyurethanes were judged by the value of a prothrombin index.

Given below is a method of determining the prothrombin index, which method is a modification of the well-known Lindholm method.

The carry out the above method, use was made of a device constructed at the Institute of Macromolecular Chemistry of Czechoslovak Academy of Sciences/G. Drobnik, M. Stol, G. Dvorakova, G. Kalal and Z. Vorlova, Thrombogenicity of alloplastic materials: in vitro testing in a planepaved chamber, 17-th microsymposium of macromolecules. Medical Polymers: Prague, 63, 1977/, which comprises a pipe for feeding a liquid and six removable chambers connected with said pipe through respective connecting pieces provided with seals. One end of said pipe is adapted to be connected to the donor and the other one is provided with a seal and serves to check up the level of filling of the described device. All the metal portions of the device are covered with silicone.

18 hours before the experiment, samples to be treated were placed into chambers, whereupon the device was filled up with the Ringer solution.

Just before the experiment, the device was connected to the donor. From the donor the blood entered the chambers and expelled the Ringer solution from the device. When the chambers were filled with blood, they were detached, and the blood was incubated for 4 hours at a temperature of 37° C. The incubated blood was centrifuged, and the obtained serum was used for further investigations. For this purpose, the serum was taken by a polypropylene syringe and centrifuged in glass test tubes at a speed of 2000 rotations per minute. The obtained superdeposit liquid was cooled down on an ice bath and used in investigation procedures. The incubation mixture comprised 0.1 ml of serum and 0.1 ml of tissue thromboplastin. Said mixture was incubated for 1 minute at a temperature of 37° C., whereupon 0.2 ml of deprothrombin plasma was added thereto, and the time of formation of the first fibrinous threads, i.e. prothrombin time, or prothrombin index, was determined. The less is the value of the prothrombin index, the better are the thromboresistant properties of the material.

There were carried out control tests wherein the following materials were used: glass as a thrombogenic material and glass covered with hydron as a nonthrombogenic material.

The results of determination of the prothrombin index are given in Table 8.

TABLE 9

| No. | Tested material | Number of tests | Prothrombin index, sec |
|---|---|---|---|
| 1 | Polyurethane urea acyl semicarbazide No. 11 in accordance with Table 1 | 3 | 37.8 ± 1.6 |
| 2 | Polyurethane urea acyl semicarbazide No. 2 in accordance with Table 1 | 3 | 45.3 ± 3.8 |
| 3 | Glass | 6 | 180 |
| 4 | Hydron | 6 | 31.4 ± 2.5 |

DETAILED DESCRIPTION OF THE INVENTION

The polyurethanes of the present invention are produced in the result of the interaction between a prepolymer containing at least two isocyanate groups and a hydrazide of an amino acid or peptide in a solvent at an equimolecular ratio of reagents at a temperature of 20° to 25° C.

The method is carried out in the following way.

As an initial product there are used hydrazides of amino acids or peptides.

These compounds are obtained from hydrazides of N-carbobenzoxy amino acids and hydrazides of N-carbobenzoxy peptides by removing N-carbobenzoxy groups with a 2 N solution of hydrogen bromide in a glacial acetic acid. Said hydrazides can be obtained by other methods as well /see, for instance, F. Weygand, W. Swodenk, N-TFA-Aminosäurehydrazide aus den Methylestern und Diketopiperazin-bildung aus N-TFA-Dipeptid-methylestern mit Hydrazin, Chem. Ber., 93, 1693–1696, 1960; K. Hofmann, A. Lindemann, M. Z. Magee, N. H. Khan. Studies on Polypeptides, III Novel Routes to α-Amino Acid and Polypeptide Hydrazides, J.Am. Chem. Soc., 74, 470–475, 1952/.

Said hydrazide is dissolved. As a solvent there may be used dimethyl formamide, hexamethyl phosphoric triamide or dimethyl sulfoxide as well as a mixture of said solvents with dioxane or ethyl acetate in the ratio of 1:1. The solution of hydrazide of an amino acid or peptide in one of said solvents is prepared in the following way.

Dibromohydrate of hydrazide of an amino acid or of peptide (0.1 to 0.2 mole) is dissolved in 20 to 30 ml of one of said solvents, whereupon triethylamine (0.2 to 0.4 mole) is added to the obtained mixture as an acceptor of hydrogen bromide. The precipitated of triethylamine bromohydrate is filtered out and washed with 15 to 20 ml of the solvent being used. The obtained solution of hydrazide of an amino acid or of peptide is added dropwise to a solution of a prepolymer in the solvent (80–160 ml) being used, the latter solution being continuously stirred. The temperature of the reaction mixture should be within the range of 20° to 25° C.

To prepare the polyurethane of the present invention, there may be used prepolymers:

based on polyoxytetramethylene glycol having a molecular mass of 1000 and hexamethylene diisocyanate;

based on polyoxytetramethylene glycol having a molecular mass of 1000 and diphenylmethane diisocyanate;

based on polyoxytetramethylene glycol having a molecular mass of 1500 and hexamethylene diisocyanate.

Said prepolymers are obtained in the result of interaction between hydroxyl containing compounds (polyethers) and diisocyanates in a molar ratio of 1:2 at a temperature of 70° C. in an atmosphere protected against moisture. The reaction was considered to be over as soon as the theoretic value of the content of isocyanate groups in the polymer was attained. The content of isocyanate groups in the reaction mixture was determined with the aid of the Stagg method /S. Stagg, Analyst, 71, 5571 (1946)/ which consists in the reaction between a sample being analyzed (weighed portion of 0.1 to 0.2 g) and the excess of 0.1 N solution of aliphatic amine in toluene or in chlorobenzene. The excess of said amine is titrated with an aqueous solution of an 0.1 N hydrochloric acid. The percentage of isocyanate groups in the polymer is determined from the following formula:

$$\% \text{ NCO} = \frac{0.42 \, (v_0 - v_1)}{g}$$

where $v_0$ volume of the 0.1 N hydrochloric acid spent for the titration of an aliquot of the 0.1 N solution of aliphatic amine in toluene (ml);

$v_1$ volume of the 0.1 N hydrochloric acid spent for the titration of an aliquot of the 0.1 N solution of aliphatic amine in toluene with dissolved therein weighed portion of the sample being analyzed (ml);

g weighed portion of the sample being analyzed (g).

The reaction solution of polyurethane urea acyl semicarbazide, prepared as described above is held for 18 hours, whereupon, under continuous stirring, it is poured into a vessel containing cold water. As a result, the end product precipitates in the form of white crumbs or flakes. The precipitated end product is filtered out, washed with water in order to eliminate the odor of the solvent, and dried to the constant weight at a temperature of 40° C.

The yield of the end product is from 90.1 to 97.9%.

Thus, polyurethanes are prepared comprising the links of natural compounds, namely α-L-amino acids and peptides in the main polymer chain. Such hydride polymers are susceptible to specific influence of proteolytic enzymes and tissue cathepsins.

A collection of the proposed polyurethanes having a particular rate of biodegradation makes it possible to accurately control the process of biodegradation of alloimplants prepared from such polyurethanes, taking into account the enzymous composition of tissues. The control of the biodegradation process is accomplished by means of mixing said polyurethanes in an appropriate ratio.

A fuller understanding of the nature of the invention will be had from the following description of Examples thereof.

EXAMPLE 1

Polyurethane urea acyl semicarbazide No. 1, as numbered in Table 1, was obtained according to the invention in the following way.

1.35 g (0.00505 mole) of L-alanine hydrazide dibromohydrate was dissolved in 10 ml of dimethyl formamide, whereupon 1.41 ml (0.0101 mole) of triethylamine was added thereto. In 15 minutes the precipitated triethylamine bromohydrate was filtered out and washed in 10 ml of dimethyl formamide. The obtained solution of L-alanine hydrazide was added dropwise to a solution of 6.75 g (0.00505 mole) of the prepolymer, based on polyoxytetramethylene glycol having a molecular mass of 1000 and on hexamethylene diisocyanate, in 40 ml of dimethyl formamide, the latter solution being continuously stirred. Thus obtained reaction solution was held for 18 hours, whereupon, under continuous stirring, it was poured into a vessel containing cold water in an amount of 0.6 l. As a result, the end product precipitated in the form of white flakes. The precipitated end product was filtered out, deodorized with water from the scent of dimethyl formamide, and then dried to the constant weight at a temperature of 40° C. The yield of the end product was 6.5 g (91.2%).

EXAMPLE 2

Polyurethane urea acyl semicarbazide No. 2, in compliance with Table 1, was obtained according to the invention in the following way.

3.51 g (0.0103 mole) of L-phenylalanine hydrazide dibromohydrate was dissolved in 25 ml of dimethyl formamide, whereupon 2.88 ml (0.0206 mole) of triethylamine was added thereto. In 15 minutes the precipitated triethylamine bormohydrate was filtered out and washed in 15 ml of dimethyl formamide. The obtained solution L-phenylalanine hydrazide was added dropwise to a solution of 13.82 g (0.0103 mole) of the prepolymer, based on polyoxytetramethylene glycol having a molecular mass of 1000 and on hexamethylene diisocyanate, in 75 ml of dimethyl formamide the latter solution being continuously stirred.

Thus obtained reaction solution was held for 18 hours, whereupon, under continuous stirring, it was poured into a vessel containing cold water in an amount of 1.0 l. As a result, the end product precipitated in the form of white flakes. The precipitated end product was filtered out, deodorized with water from the scent of dimethyl formamide, and then dried to the constant weight at a temperature of 40° C. The yield of the end product was 14.5 g (92.5%).

EXAMPLE 3

Polyurethane urea acyl semicarbazide No 3, in compliance with Table 1, was prepared according to the invention in the following way.

7.31 g (0.0248 mole) of O-acetyl-L-serine hydrazide dibromohydrate was dissolved in 25 ml of dimethyl formamide, whereupon 6.92 ml (0.0496 mole) of triethylamine was added thereto. In 15 minutes the precipitated triethylamine bromohydrate was filtered out and washed with dimethyl formamide taken in an amount of 15 ml. The obtained solution of O-acetyl-serine hydrazide was added dropwise to a solution of 33.18 g (0.0248 mole) of the prepolymer, based on polyoxytetramethylene glycol having a molecular mass of 1000 and on hexamethylene diisocyanate, in 120 ml of dimethyl formamide. As this took place, the prepolymer solution was continuously stirred.

Thus obtained reaction solution was held for 18 hours, whereupon, under continuous stirring, it was poured into a vessel containing cold water in an amount of 1.5 l. As a result, the end product precipitated in the form of white flakes. The precipitated end product was filtered out, deodorized with water from the scent of dimethyl formamide, and then dried to the constant weight at a temperature of 40° C. The yield of the end product was 32.8 g (90.1%).

EXAMPLE 4

Polyurethane urea acyl semicarbazide No. 4, in compliance with Table 1, was prepared according to the invention in the following way.

3.08 g (0.0100 mole) of L-leucine hydrazide dibromohydrate was dissolved in 20 ml of dimethyl formamide, whereupon 2.78 ml (0.0200 mole) of triethylamine was added thereto. In 15 minutes the precipitated triethylenamine bromohydrate was filtered out and washed with dimethyl formamide taken in an amount of 10 ml. The obtained solution of L-leucine hydrazide was added dropwise to a solution of 13.36 g (0.0100 mole) of the prepolymer, based on polyoxytetramethylene glycol having a molecular mass of 1000 and on hexamethylene diisocyanate, in 70 ml of dimethyl formamide. As this took place, the prepolymer solution was continuously stirred.

Thus obtained reaction solution was held for 18 hours, whereupon, under continuous stirring, it was poured into a vessel containing cold water in an amount of 1.0 l.

As a result, the end product precipitated in the form of white flakes.

The precipitated end product was filtered out, doedorized with water from the scent of dimethyl formamide, and then dried to the constant weight thereof at a temperature of 40° C.

The yield of the end product was 13.4 g (90.4%).

EXAMPLE 5

Polyurethane urea acyl semicarbazide No. 5, in compliance with Table 1, was prepared according to the invention in the following way.

6.80 g (0.0200 mole) of L-methionine hydrazide dibromohydrate was dissolved in 25 ml of dimethyl formamide, whereupon 5.56 ml (0.0400 mole) of triethylamine was added thereto. In 15 minutes the precipitated triethylenamine bromohydrate was filtered out and washed with dimethyl formamide taken in an amount of 15 ml. The obtained solution of L-methionine hydrazide was added dropwise to a solution of 26.72 g (0.0200 mole) of the prepolymer, based on polyoxytetramethylene glycol having a molecular mass of 1000 and on hexamethylene diisocyanate, in 130 ml of dimethyl formamide. As this took place, the prepolymer solution was continuously stirred.

Thus obtained reaction solution was held for 18 hours, whereupon, under continuous stirring, it was poured into a vessel containing cold water in an amount of 1.5 l. As a result, the end product precipitated in the form of white flakes. The precipitated end product was filtered out, deodorized with water from the scent of dimethyl formamide, and then dried to the constant weight thereof at a temperature of 40° C.

The yield of the end product was 28.8 g (93.2%).

EXAMPLE 6

Polyurethane urea acyl semicarbazide No 6, in compliance with Table 1, was prepared according to the invention in the following way.

1.85 g (0.00518 mole) of L-tyrosin hydrozide dibromohydrate was dissolved in 15 ml of dimethyl formamide whereupon 1.44 ml (0.01036 mole) of triethylamine was added thereto. In 15 minutes the precipitated triethylenamine bromohydrate was filtered out and washed with dimethyl formamide taken in an amount of 10 ml.

The obtained L-tyrosin hydrazide solution was added dropwise to a solution of 6.97 g (0.00518 mole) of the prepolymer, based on polyoxytetramethylene glycol having a molecular mass of 1000 and on hexamethylene diisocyanate, in 55 ml of dimethyl formamide. As this took place, the prepolymer solution was continuously stirred.

Thus prepared solution was held for 18 hours, whereupon, under continuous stirring, it was poured into a vessel containing cold water in an amount of 1.0 l. As a result, the end product precipitated in the form of white flakes. The precipitated end product was filtered out, deodorized with water from the scent of dimethyl formamide, and then dried to the constant weight thereof at a temperature of 40° C.

The yield of the end product was 6.8 g (90.5%).

EXAMPLE 7

Polyurethane urea acyl semicarbazide No 7, in compliance with Table 1, was prepared according to the invention in the following way.

3.58 g (0.0200 mole) of DL-phenylalanine hydrazide was dissolved in 50 ml of dimethyl formamide and added dropwise to a solution of 26.72 g (0.0200 mole) of the prepolymer, based on polyoxytetramethylene glycol having a molecular mass of 1000 and on hexamethylene diisocyanate, in 100 ml of dimethyl formamide.

Thus obtained reaction solution was held for 18 hours, whereupon, under continuous stirring, it was poured into a vessel containing cold water in an amount of 1.5 l. As a result, the end product precipitated in the form of white flakes. The precipitated end product was filtered out, deodorized with water from the scent of dimethyl formamide, and then dried to the constant weight thereof at a temperature of 40° C.

The yield of the end product was 28.9 g (95.3%).

EXAMPLE 8

Polyurethane urea acyl semicarbazide No 8, in compliance with Table 1, was prepared according to the invention in the following way.

6.12 g (0.0200 mole) of glycyl-glycine hydrazide dibromohydrate was solved in 25 ml of dimethyl formamide, whereupon 5.54 ml (0.0400 mole) of triethylamine was added thereto. In 15 minutes the precipitated triethylamine bromohydrate was filtered out and washed with dimethyl formamide taken in amount of 25 ml.

The obtained glycyl-glycine hydrazide solution was added dropwise to a solution of 26.72 g (0.0200 mole) of the prepolymer, based on polyoxytetraethylene glycol having a molecular mass of 1000 and on hexamethylene diisocyanate, in 70 ml of dimethyl formamide. As this took place, the prepolymer solution was continuously stirred.

Thus prepared reaction solution was held for 18 hours, whereupon, under continuous stirring, it was poured into a vessel containing cold water in an amount of 1.5 l. As a result, the end product precipitated in the form of white crumbs. The precipitated end product was filtered out, deodorized with water from the scent of dimethyl formamide, and then dried to the constant weight thereof at a temperature of 40° C.

The yield of the end product was 27.7 g (93.0%).

EXAMPLE 9

Polyurethane urea acyl semicarbazide No 9, in compliance with Table 1, was prepared according to the invention in the following way.

8.81 g (0.0263 mole) of L-alanyl-L-alanine hydrozide dibromohydrate was dissolved in 25 ml of dimethyl formamide, whereupon 7.28 ml (0.0526 mole) of triethylamine was added thereto. In 15 minutes the precipitated triethylamine bromohydrate was filtered out and washed with dimethyl formamide taken in an amount of 15 ml.

The obtained L-alanyl-L-alanine hydrazide solution was added dropwise to a solution of 35.0 g (0.0263 mole) of the prepolymer, based on polyoxytetramethylene glycol having a molecular mass of 1000 and on hexamethylene diisocyanate, in 200 ml of dimethyl formamide. As this took place, the prepolymer solution was continuously stirred.

Thus prepared reaction solution was left for 18 hours, whereupon, under continuous stirring, it was poured into a vessel containing cold water in an amount of 2.0 l. As a result, the end product precipitated in the form of white crumbs. The precipitated end product was filtered out, deodorized with water from the scent of dimethyl formamide, and then dried to the constant weight thereof at a temperature of 40° C.

The yield of the end product was 36.4 (92.0%).

EXAMPLE 10

Polyurethane urea acyl semicarbazide No. 10, in compliance with Table 1, was prepared according to the invention in the following way.

13.39 g (0.0266 mole) of L-phenyl-alanyl-L-phenylalanine hydrozide dibromohydrate was dissolved in 25 ml of dimethyl formamide, whereupon 7.65 ml (0.0532 mole) of triethylamine was added thereto. In 15 minutes the precipitated triethylenamine bromohydrate was filtered out and washed with dimethyl formamide taken in amount of 20 ml.

The obtained L-phenylalanyl-L-phenylalanine hydrazide solution was added dropwise to a solution of 37.0 (0.0266 mole) of the prepolymer, based on polyoxytetramethylene glycol having a molecular mass of 1000 and on hexamethylene diisocyanate, in 130 ml of dimethyl formamide. As this took place, the prepolymer solution was continuously stirred.

Thus prepared reaction solution was left for 18 hours, whereupon, under stirring, it was poured into a vessel containing cold water in an amount of 2.0 l. As a result, the end product precipitated in the form of white flakes. The precipitated end product was filtered out, deodorized with water from the scent of dimethyl formamide, and then dried to the constant weight thereof at a temperature of 40° C.

The yield of the end product was 43.5 g (97.9%).

EXAMPLE 11

Polyurethane urea acyl semicarbazide No. 11, in compliance with Table 1, was prepared according to the invention in the following way.

17.71 g (0.0396 mole) of L-phenylalanyl-O-acetyl-L-serine hydrazide dibromohydrate was dissolved in 30 ml of dimethyl formamide, whereupon 1.10 ml (0.0792 mole) of triethylamine was added thereto. In 15 minutes the precipitated triethyleneamine bromohydrate was filtered out and washed with dimethyl formamide taken in an amount of 20 ml.

The obtained L-phenylalanyl-O-acetyl-L-serine hydrazide dibromohydrate was added dropwise to a solution of 53.0 g (0.0396 mole) of the prepolymer, based on polyoxytetramethylene glycol having a molecular mass of 1000 and on hexamethylene diisocyanate, in 270 ml of dimethyl formamide. As this took place, the prepolymer solution was stirred.

Thus prepared reaction solution was left for 18 hours, whereupon, under continuous stirring, it was poured into a vessel containing cold water in an amount of 3.0 l. As a result, the end product precipitated in the form of white crumbs. The precipitated end product was filtered out, deodorized with water from the scent of dimethyl formamide, and then dried to the constant weight thereof at a temperature of 40° C.

The yield of the end product was 55.8 g (91.2%).

EXAMPLE 12

Polyurethane urea acyl semicarbazide No. 12, in compliance with Table 1, was prepared according to the invention in the following way.

2.11 g (0.00532 mole) of L-phenylalanyl-glycine hydrazide dibromohydrate was dissolved in 15 ml of dimethyl formamide, whereupon 1.48 ml (0.01064 mole) of triethylamine was added thereto. In 15 minutes the precipitated triethylenamine bromohydrate was filtered out and washed with dimethyl formamide taken in an amount of 10 ml.

The obtained L-phenylalanyl-glycine hydrazide solution was added dropwise to a solution of 7.11 g (0.00532 mole) of the prepolymer based on polyoxytetramethylene glycol having a molecular mass of 1000 and on hexamethylene diisocyanate, in 65 ml of dimethyl formamide. As this took place, the prepolymer solution was continuously stirred.

Thus prepared reaction solution was left for 18 hours, whereupon under continuous stirring, it was poured into a vessel containing cold water in an amount of 1.0. As a result, the end product precipitated in the form of white crumbs. The precipitated end product was filtered out, deodorized with water from the scent of dimethyl formamide, and then dried to the constant weight thereof at a temperature of 40° C.

The yield of the end product was 7.6 g (91.6%).

EXAMPLE 13

Polyurethane urea acyl semicarbazide No. 13, in compliance with Table 1, was prepared according to the invention in the following way.

2.35 g (0.0050 mole) of L-alanyl-L-phenylalanylglycine hydrazide dibromohydrate was dissolved in 20 ml of dimethyl formamide, whereupon 1.39 ml (0.0100 mole) of triethylamine was added thereto. In 15 minutes the precipitated triethylamine bromohydrate was filtered out and washed with dimethyl formamide taken in an amount of 10 ml.

The obtained L-alanyl-L-phenylalanyl-glycine solution was added dropwise to a solution of 6.68 g (0.0050 mole) of the prepolymer, based on polyoxytetramethylene glycol having a molecular mass of 1000 and on hexamethylene diisocyanate, in 40 ml of dimethyl formamide for 40 minutes. As this took place, the prepolymer solution was continuously stirred.

Thus prepared reaction solution was left for 18 hours, whereupon, under continuous stirring, it was poured into a vessel containing cold water in an amount of 0.7 l. As a result the end product precipitated in the form of white crumbs. The precipitated end product was filtered out, deodorized with water from the scent of dimethyl formamide, and then dried to the constant weight thereof at a temperature of 40° C.

The yield of the end product was 8.2 g (99.3%).

EXAMPLE 14

Polyurethane urea acyl semicarbazide No. 14, in compliance with Table 1, was prepared according to the invention in the following way.

0.80 g (0.0030 mole) of L-alanine hydrazide dibromohydrate was dissolved in 20 ml of dimethyl formamide, whereupon 0.84 ml (0.0060 mole) of triethylamine was added thereto. In 15 minutes the precipitated triethylamine bromohydrate was filtered out and washed with dimethyl formamide taken in an amount of 10 ml. The obtained L-alanine hydrazide solution was added dropwise during 30 minutes to a solution of 4.50 g (0.0030 mole) of the prepolymer, based on polyoxytetramethylene glycol having a molecular mass of 1000 and on diphenylmethane diisocyanate, in 30 ml of dimethyl formamide at a temperature of 25° C. As this took place, the prepolymer solution was continuously stirred.

Thus prepared reaction solution was left for 12 hours, whereupon, under continuous stirring, it was poured into a vessel containing cold water in an amount of 0.6 l.

As a result, the end product precipitated in the form of large white flakes. The precipitated end product was filtered out, deodorized with water from the scent of dimethyl formamide, and then dried to the constant weight thereof at a temperature of 40° C.

The yield of the end product was 4.4 g (91.54%).

EXAMPLE 15

Polyurethane urea acyl semicarbazide No. 15, in compliance with Table 1, was prepared according to the invention in the following way.

6.60 g (0.0193 mole) of L-phenylalamine hydrazide dibromohydrate was dissolved in 50 ml of dimethyl formamide, whereupon 5.36 ml (0.0386 mole) of triethylamine was added thereto. In 10 minutes the precipitated triethylamine bromohydrate was filtered out and washed with dimethyl formamide taken in an amount of 25 ml. The obtained L-phenylalamine hydrazide solution was added dropwise to a solution of 28.95 g (0.0193 mole) of the prepolymer, based on polyoxytetramethylene glycol having a molecular mass of 1000 and on diphenylmethane diisocyanate, in 100 ml of dimethyl formamide. As this took place, the prepolymer solution was continuously stirred.

Thus prepared reaction solution was left for 12 hours, whereupon, under continuous stirring, it was poured into a vessel containing cold water in an amount of 2.0 l. As a result, the end product precipitated in the form of white flakes. The precipitated end product was filtered out, deodorized with water from the scent of dimethyl formamide, and then dried to the constant weight thereof at a temperature of 40° C.

The yield of the end product was 29.5 g (91.0%).

EXAMPLE 16

Polyurethane urea acyl semicarbazide No. 16, in compliance with Table 1 was prepared according to the invention in the following way.

2.0 g (0.0071 mole) of L-serine hydrazide dibromohydrate was dissolved in 20 ml of dimethyl formamide, whereupon 1.98 ml (0.0142 mole) of thriethylamine was added thereto. In 15 minutes the precipitated triethylamine bromohydrate was filtered out and washed with dimethyl formamide taken in an amount of 10 ml. The obtained L-serine hydrazide solution was added dropwise, during 30 minutes, to a solution of 10.65 g of the prepolymer, based on polyoxytetramethylene glycol having a molecular mass of 1000 and on diphenylmethane diisocyanate, in 40 ml of dimethyl formamide at a temperature of 25° C. As this took place, the prepolymer solution was continuously stirred.

Thus prepared reaction solution was left for 12 hours, whereupon, under continuous stirring, it was poured into a vessel containing cold water in an amount of 0.7 l. As a result, the end product precipitated in the form of white flakes. The precipitated end product was filtered out, deodorized with water from the scent of dimethyl formamide, and then dried to the constant weight thereof at a temperature of 40° C.

The yield of the end product was 10.8 g (93.9%).

EXAMPLE 17

Polyurethane urea acyl semicarbazide No. 17, in compliance with Table 1, was prepared according to the invention in the following way.

3.23 g (0.010 mole) of O-acetyl-L-serine hydrazide dibromohydrate was dissolved in 20 ml of dimethyl formamide, whereupon 2.78 ml (0.020 mole) of triethylamine was added thereto. In 15 minutes the precipitated triethylamine bromohydrate was filtered out and washed with dimethyl formamide taken in an amount of 10 ml.

The obtained O-acetyl-L-serine hydrazide solution was added dropwise to a solution of 15.0 g (0.010 mole) of the prepolymer based on polyoxytetramethylene glycol having a molecular mass of 1000 and on diphenylmethane diisocyanate in 100 ml of dimethyl formamide. As this took place, the prepolymer solution was continuously stirred.

Thus prepared reaction solution was left for 12 hours, whereupon, under continuous stirring, it was poured into a vessel containing cold water in an amount of 1.5 l. As a result, the end product precipitated in the form of white flakes. The precipitated end product was filtered out, deodorized with water from the scent of dimethyl formamide, and then dried to the constant weight thereof at a temperature of 40° C.

The yield of the end product was 16.7 g (96.3%).

EXAMPLE 18

Polyurethane urea acyl semicarbazide No. 18, in compliance with Table 1, was prepared according to the invention in the following way.

1.00 g (0.0029 mole) of L-alanyl-L-alanine hydrazide dibromohydrate was dissolved in 15 ml of dimethyl formamide, whereupon 0.80 ml (0.0058 mole) of triethylamine was added thereto. In 15 minutes the precipitated triethylamine bromohydrate was filtered out and washed with dimethyl formamide taken in an amount of 10 ml.

The obtained L-alanine-L-alanine hydrazide solution was added dropwise, during 30 minutes, to a solution of 4.34 g (0.0029 mole) of the prepolymer, based on polyoxytetramethylene glycol having a molecular mass of 1000 and on diphenylmethane diisocyanate, in 30 ml of dimethyl formamide at a temperature of 25° C. As this took place, the prepolymer solution was continuously stirred.

Thus prepared reaction solution was left for 12 hours, whereupon, under continuous stirring, it was poured into a vessel containing cold water in an amount of 0.5 l. As a result, the end product precipitated in the form of white flakes. The precipitated end product was filtered out, deodorized with water from the scent of dimethyl formamide, and then dried to the constant weight thereof at a temperature of 40° C.

The yield of the end product was 4.4 g (90.6%).

EXAMPLE 19

Polyurethane urea acyl semicarbazide No. 19, in compliance with Table 1, was prepared according to the invention in the following way.

7.0 g (0.0143 mole) of L-phenylalanyl-L-phenylalanine hydrozide dibromohydrate was dissolved in 30 ml of dimethyl formamide, whereupon 3.98 ml (0.0286 mole) of triethylamine was added thereto. In 15 minutes the precipitated triethylamine bromohydrate was filtered out and washed with dimethyl formamide taken in amount of 20 ml. The obtained L-phenylalanyl-L-phenylalanine was added dropwise, during 30 to 40 minutes, to a solution of 21.47 g (0.0143 mole) of the prepolymer, based on polyoxytetramethylene glycol having a molecular mass of 1000 and on diphenylamethane diisocyanate, in 100 ml of dimethyl formamide. As this took place, the prepolymer solution was continuously stirred.

Thus prepared reaction solution was left for 12 hours, whereupon, under continuous stirring, it was poured into a vessel containing cold water in an amount of 1.5 l. As a result, the end product precipitated in the form of white flakes. The precipitated end product was filtered out, deodorized with water from the scent of dimethyl formamide, and then dried to the constant weight thereof at a temperature of 40° C.

The yield of the end product was 23.7 g (90.7%).

EXAMPLE 20

Polyurethane urea acyl semicarbazide No. 20, in compliance with Table 1, was prepared according to the invention in the following way.

2.50 g (0.0063 mole) of L-phenylalanyl-glycine hydrazide dibromohydrate was dissolved in 20 ml of dimethyl formamide, whereupon 1.74 g (0.0126 mole) of triethylamine was added thereto. In 15 minutes the precipitated triethylamine bromohydrate was filtered out and washed with dimethyl formamide taken in an amount of 10 ml. The obtained L-phenyl-alanyl-glycine hydrazide solution was added dropwise, during 30 minutes, to a solution of 9.42 g (0.0063 mole) of the prepolymer, based on polyoxytetramethylene glycol having a molecular mass of 100 and on diphenylmethane diisocyanate, in 35 ml of dimethyl formamide. As this took place, the prepolymer solution was continuously stirred at a temperature of 25° C.

Thus prepared reaction solution was left for 12 hours, whereupon, under continuous stirring, it was poured into a vessel containing 0.7 ml of cold water. As a result, the end product precipitated in the form of white flakes. The precipitated end product was filtered out, deodorized with water from the scent of dimethyl formamide, and then dried to the constant weight thereof at a temperature of 40° C.

The yield of the end product was 10.5 g (96.04%).

EXAMPLE 21

Polyurethane urea acyl semicarbazide No. 21, in compliance with Table 1, was prepared according to the invention in the following way.

2.00 g (0.0048 mole) of L-alanyl-L-phenylalanylglycine hydrazide dibromohydrate was dissolved in 20 ml of dimethyl formamide, whereupon 1.32 ml (0.0096 mole) of triethylamine was added thereto. In 15 minutes the precipitated triethylamine bromohydrate was filtered out and washed with dimethyl formamide taken in an amount of 15 ml. The obtained L-alanyl-L-phenylalanyl-glycine hydrazide solution was added dropwise, during 40 minutes, to a solution of 7.16 g (0.0048 mole) of the prepolymer, based on polyoxytetramethylene glycol having a molecular mass of 1000 and on diphenylmethane diisocyanate, in 50 ml of diphenyl formamide at a temperature of 25° C. As this took place, the prepolymer solution was continuously stirred.

Thus prepared reaction solution was left for 12 hours, whereupon, under continuous stirring, it was poured into a vessel containing 0.1 l of cold water. As a result, the end product precipitated in the form of white flakes. The precipitated end product was filtered out, deodorized with water from the scent of dimethyl formamide, and then dried to the constant weight thereof at a temperature of 40° C.

The yield of the end product was 8.0 g (92.2%).

EXAMPLE 22

Polyurethane urea acyl semicarbazide No. 22, in compliance with Table 1, was prepared according to the invention in the following way.

2.37 g (0.0069 mole) of L-phenyl-alanine hydrazide dibromohydrate was dissolved in 20 ml of dimethyl formamide, whereupon 2.93 ml (0.0138 mole) of triethylamine was added thereto. In 15 minutes the precipitated triethylamine bromohydrate was filtered out and washed with dimethyl formamide taken in an amount of 15 ml. The obtained L-phenylalanine hydrazide solution was added dropwise, during 30 minutes, to a solution of 12.74 g (0.0069 mole) of the prepolymer, based on polyoxytetramethylene glycol having a molecular mass of 1500 and on hexamethylene diisocyanate, in 50 ml of diphenyl formamide at a temperature of 20° to 25° C. As this took place, the prepolymer solution was continuously stirred.

Thus prepared reaction solution was left for 12 hours, whereupon, under continuous stirring, it was poured into a vessel containing 1.0 l of cold water. As a result, the end product precipitated in the form of white flakes. The precipitated end product was filtered out, deodorized with water from the scent of dimethyl formamide, and then dried to the constant weight thereof at a temperature of 40° C.

The yield of the end product was 13.3 g (95.1%).

While particular embodiments of the invention have been shown and described, various modifications thereof will be apparent to those skilled in the art and therefore it is not intended that the invention be limited to the disclosed embodiments and the departures may be made therefrom within the spirit and scope of the invention as defined in the claims.

We claim:

1. Polyurethane urea acyl semicarbazides for preparing biodegradable alloimplants having the general formula: $(-NH-R_1-CONHNHCONH-R_2-NH-CO-O-R_3-CONH-R_2-NH-CO-)_n$ $R_1$ is selected from the group consisting of

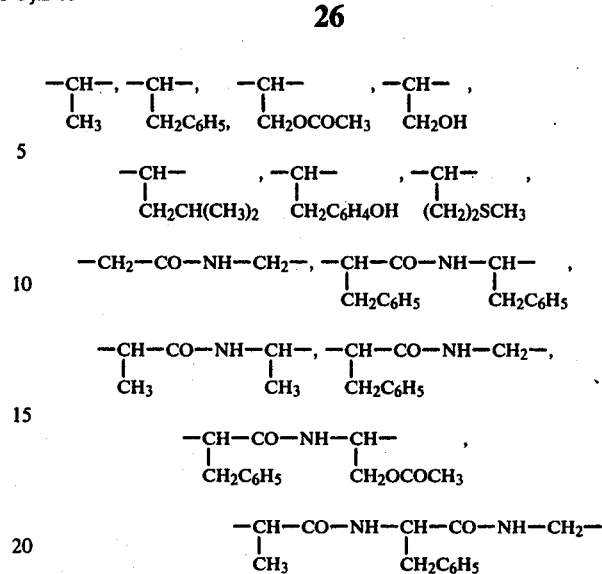

wherein n is from 5 to 24 $R_2$ is selected from the group consisting of $-(CH_2)_6-$, $-C_6H_4-CH_2-C_6H_4$;

$R_3$ is selected from the group consisting of $-(CH_2)_4-O-_{14}$, $-(CH_2)_4-O-_{21}$.

2. A biodegradable implant comprising a polyurethane urea acyl semicarbazide as defined in claim 1.

* * * * *